United States Patent [19]

Gray et al.

[11] 4,277,560
[45] Jul. 7, 1981

[54] ENZYME IMMUNOASSAYS USING IMMOBILIZED REAGENTS IN A FLOWING STREAM

[75] Inventors: Don N. Gray; Melvin H. Keyes, both of Sylvania, Ohio

[73] Assignee: Technicon Instruments Corporation, Tarrytown, N.Y.

[21] Appl. No.: 954,269

[22] Filed: Oct. 24, 1978

[51] Int. Cl.$^3$ ................ C12M 1/34; G01N 33/54; G01N 21/00
[52] U.S. Cl. ............................... 435/7; 435/291; 23/230 B; 424/12; 422/81
[58] Field of Search .............. 435/4, 7, 288, 291, 435/14; 204/195 B; 23/230 B; 422/68, 63, 67, 71, 81, 82, 101; 424/12

[56] References Cited

U.S. PATENT DOCUMENTS

| | | | |
|---|---|---|---|
| 3,902,970 | 9/1975 | Levin | 435/14 |
| 3,925,018 | 12/1975 | Saunders | 435/7 |
| 3,975,237 | 8/1976 | Rubenstein | 435/7 |
| 3,993,451 | 11/1976 | Verbeck | 435/14 |
| 4,009,005 | 2/1977 | Johnson | 422/71 |
| 4,022,577 | 5/1977 | Brooker et al. | 23/230 B |
| 4,125,492 | 11/1978 | Cuatrecasas et al. | 210/31 C |
| 4,141,687 | 2/1979 | Forrest et al. | 435/7 |
| 4,200,625 | 4/1980 | Reese | 23/230 B |

OTHER PUBLICATIONS

Ishikawa, "Enzyme Immunoassay of Insulin by Fluorimetry of the Insulin–Glucoamylase Complex," *J. Biochem.*, vol. 73, No. 6, (1973), pp. 1319-1321.
Ismail et al., "The South Mend System," A Simple, Fully-Automated, Continuous-Flow System for Immunoassays [Appendix: Application to Serum Thyromine Radioimmunoassay], *Clin. Chem.*, vol. 24, No. 4, (1978), pp. 571-579.
Brooker et al., "Gammaflow: A Completely Automated Radioimmunoassay System," *Science*, vol. 194, (1976), pp. 270-276.

*Primary Examiner*—Thomas G. Wiseman
*Attorney, Agent, or Firm*—Morgan, Finnegan, Pine, Foley & Lee

[57] ABSTRACT

This invention relates to a method and apparatus for the rapid quantitative determination of an antigen contained in aqueous biochemical samples, for example, blood. The method comprises a series of sequentially arranged stages through which a buffered stream flows. The sample, containing an unknown concentration of the antigen, is injected into the buffered flowing stream and contacts various reagents in the sequential series of stages. An initial solubilization stage comprises an immobilized antibody on a substrate which antibody is specific to the antigen in the sample. The immobilized antibody has been reacted previously to saturation with an enzyme-antigen complex, the antigen of the complex being the same as the antigen in the sample, and the complex is reversably bound to the immobilized antibody. The antigen in the sample and buffered stream flow through the solubilization stage and a competitive equilibrium reaction takes place between the complex bound to the antibody and the antigen in the sample, resulting in the release of a quantity of the enzyme-antigen complex into the flowing stream. The complex and the stream pass into a conversion stage wherein the complex reacts with an immobilized substrate, such as starch, to produce a measurable product which is a quantitative index of the complex released in the solubilization stage. The measurable product and the stream flow to a detection stage wherein the product is reacted, quantitatively measured and related to the concentration of the antigen in the original sample.

24 Claims, 3 Drawing Figures

FIG. 3

ENZYME IMMUNOASSAYS USING IMMOBILIZED REAGENTS IN A FLOWING STREAM

BACKGROUND OF THE INVENTION

1. Field of the Invention

This invention relates to a method and apparatus for the rapid quantitative determination of biochemical antigens contained in aqueous solutions, particularly in biochemical fluids such as blood serum, urine, and also in food preparations and medicaments.

Antigens, such as the anti-convulsants, cardiovascular medicines, and toxic drugs (such as heroine, cocaine, etc.), are generally quantitatively determined by known, complex and time consuming experimental procedures. For the quantitative determination of substances involved in biochemical processes, e.g. lower molecular weight substances, such as vitamins and steroids, or e.g. higher molecular weight substances, such as proteins or carbohydrates, it is often possible to employ the reaction products of these substances with specific binding partners, particularly proteins, for which they have chemical affinities. Therefore, it is possible to determine the concentration of drugs, such as steroids, heroine, cocaine, anticonvulsants, etc., by employing a protein capable of specifically binding with the particular drug. One example of a drug commonly assayed biochemically is insulin.

It is also possible to chemically link low molecular weight substances to a protein and to inject the complex into a test animal. The test animal reacts by producing an antibody to the low molecular weight substance. Alternatively, the low molecular weight substance, known as an antigen, may be injected directly into the test animal which will again produce an antibody to the antigen. Similarly, high molecular weight substances, such as proteins and carbohydrates, are capable of causing the production of antibodies when injected into test animals. Both low and high molecular weight antigens can cause the production of specific binding partners, always proteins, which are known as antibodies.

Immunoassays methodology has been shown to be extremely versatile in allowing for the quantification of both low and high molecular weight substances, even when a wide variety of other materials chemically similar to the desired unknown are present in the unknown sample. As stated above, immunoassay methodology relies upon the ability of antibodies to specifically combine with antigens. Various immunoassay methods currently are in use, e.g. radioimmunoassay, spin immunoassay, homogeneous enzyme immunoassay, and hemeagglutination.

Radioimmunoassays require equipment and radioisotopes, which are relatively expensive.

The known enzyme immunoassays systems are extremely versatile in permitting both spectrophotometric and electrochemical determinations to be carried out. Immunoassay systems employ an enzyme, which is a catalytically active protein, to which there is complexed the antigen to be determined. The antigen-enzyme complex is bound to an antibody, thereby substantially reducing the enzyme activity of the complexed enzyme. Therefore, in a homogeneous system, by adding the unknown sample of the antigen, allowing the antigen to compete for binding sites on the antibody with the complexed enzyme, and tracing the rise in enzymatic activity, one may quantify the concentration of the unknown antigen contained in the sample. Unfortunately, even enzyme immunoassays sometimes take long periods of time and involve the use of an expensive antibody which is frequently discarded as part of the immunoassay quantification procedure.

The present invention circumvents the time and expense of previous immunoassay methods.

2. Description of the Prior Art

Procedures are known where antigens are quantified using primarily two experimental methods. The first method involves the so-called homogeneous immunoassay technique, wherein an antigen or antibody, both in soluble form, are mixed to allow the specific binding reaction to proceed, and then detection proceeds in any of a variety of procedures. The second method for the detection of antigens is the so-called heterogeneous immunoassay method wherein one of the binding partners, either the antigen or antibody, is immobilized on a solid support and reacts with the other binding partner. Then, either the solid support or the liquid is separated from the other phase and subjected to analysis. Both homogeneous and heterogeneous immunoassays are commonly described in the art and are exemplified by U.S. Pat. Nos. Re. 29,169, 3,654,090 and 3,875,011.

U.S. Pat. No. Re. 29,169 discloses the reaction between a specific binding protein and its specific binding partner. One of the binding partners is immobilized and the assay is conducted by allowing the binding to take place, separating the solid phase from the reaction mixture containing the immobilized binding partner, reacting with an enzyme the solid phase which contains a determined amount of a coupling product of the substance to be determined, and subsequently performing an enzymatic assay on either the liquid or solid phase of the reaction mixture to obtain a quantitative indication of the amount of the specific binding partner.

U.S. Pat. No. 3,654,090 discloses an antigen-antibody reaction sequence wherein one component is immobilized and the other is covalently linked to an enzyme. By the addition of one component to the other, the amount of soluble or insoluble enzyme-labelled component may be determined in relatively small quantities. Similarly, U.S. Pat. No. 3,875,011 discloses a conjugated enzyme composition useful in homogeneous enzyme immunoassays. The drug to be determined is conjugated to glucose-6-phosphate dehydrogenase. The resulting product has a relatively high substrate turnover rate and provides enzyme magnification when employed in homogeneous immunoassays.

Many techniques are known in the prior art to determine the products of either a homogeneous or heterogeneous enzyme immunoassay procedure. For example, U.S. Pat. No. 3,876,504 discloses a method for determining antigens and antibodies in human body fluids, wherein one component of the reaction is immobilized on a glass microscope type slide, flooded with a test reagent containing the other component, and bonded to a color forming agent. By monitoring the colorimetric reaction which takes place, quantification of the antigens and antibodies is possible. U.S. Pat. No. 3,555,143 discloses a process wherein water insoluble polymers are used to insolubilize antibodies. The antigen is linked to a radioactive isotope and the antigen and antibody are allowed to react in a reaction medium. Subsequently, the antibody attached to the insoluble polymers are separated from the reaction medium and the radioactivity of the antigen isotope-antibody is determined as a quantitative measure of the antigen present. A fluorimetric method of antigen immunoassay is disclosed by Eiji Ishikawa in an article entitled, "Enzyme Immunoassay of Insulin by Fluorimetry of the Insulin-glucoamylase Complex," *J. Biochem.*, V. 73, No. 6, 1319-1321 (1973). In this article, immunoassay methods may be applied using fluorimetric sensors as opposed to the traditionally accepted radionuclide methods which are expensive, and also sometimes hazardous when not properly conducted. The article also discloses another method for the chemical linking of an antigen to an enzyme.

A flow-through enzymatic reactor is disclosed in U.S. Pat. No. 3,838,011 wherein enzymatically reactive substances are contained in an aqueous solution, and are quantitatively determined by introducing a sample into a stream which flows at a constant velocity through an enzyme reactor and then through a detector system. Similarly U.S. Pat. No. 4,039,652 discloses a flow system which comprises essentially a syringe filled with immobilized antigen or antibody, wherein the non-immobilized binding partner is placed over the immobilized partner in a supernatant liquid and after a sufficient reaction time has passed, the fluid is drained from the syringe. The eluted fluid is subjected to a determination of the relative amount of the labeled compound retained or eluted from the column.

SUMMARY OF THE INVENTION

An object of this invention is to provide a method and apparatus for the quantitative determination of an antigen in biochemical fluids.

Another object of this invention is to provide a method and apparatus for the rapid quantitative determination of an antigen contained in a sample biochemical fluid by passing the sample through a series of sequential stages wherein the antigen reacts with reagents to obtain a measurable product which is quantitative index of the concentration of the antigen in the sample.

A further object of this invention is to provide an immobilized antibody, reactable with an antigen in a biochemical sample, which is saturated with an enzyme-antigen complex, wherein the antigen in the sample reacts with the immobilized antibody-complex to produce an equilibrium state between the antigen in the sample and the antigen complex whereby an amount of the complex is released into the sample and can be measured to give a quantitative index of the concentration of the antigen originally in the sample.

Another object of this invention is to provide a method and apparatus for the quantitative determination of an antigen in a biochemical sample wherein the sample is injected into a buffered flowing aqueous stream which is sequentially contacted and reacted in a series of stages to produce a measurable product which is detected and measured in a detection stage to give a quantitative determination of the concentration of the antigen in the original sample.

An additional object of the invention is to provide an apparatus which allows the rapid, low cost analysis of antigens in biochemical samples without the necessity of discarding valuable antibodies after each analysis.

The above and other objects of the invention are achieved by a method and apparatus which provides for the rapid flow-through determination of antigens in biochemical fluids using a flow-through system design. The system comprises immobilized reagents which are stable for long periods of time and are not discarded as is the case with present heterogeneous and homogeneous antigen assay procedures. The invention produces a quantitative measure of the quantity of antigen in a fluid sample by passing the sample through a solubilization stage, wherein an antigen-enzyme complex is reversibly bound to an immobilized antibody. The complex is liberated into the flowing stream by competitive equilibrium with the antigen in the unknown sample. The sample flows from the solubilization stage to a conversion stage, wherein the antigen-enzyme complex is caused to react with a substrate of the enzyme to thereby form a measurable product. The measurable product then flows to a detection stage comprising detection means which senses the concentration of the measurable product in the flowing stream. The detection means generates a signal which is communicated to readout means which quantitatively represents the concentration of the antigen in the sample.

BRIEF DESCRIPTION OF THE DRAWINGS

Other objects and advantages of the invention will become readily manifest to those skilled in the art from a reading of the following detailed description of the invention when considered with the accompanying drawings in which.

DETAILED DESCRIPTION OF THE INVENTION

The method and apparatus according to the present invention provides for the quantitative determination of an antigen in biochemical fluids, particularly in human body fluids. The invention generally comprises a unique three stage flow-through system comprising solubilization, conversion and detection stages. In the solubilization stage, an immobilized antibody specific to the antigen to be determined, is saturated with an enzyme-labelled antigen, wherein the antigen is the same as the antigen to be determined. The sample containing an unknown quantity of the antigen is introduced into a flowing stream of buffered solution which carries it into the solubilization stage. Therein the antigen in the sample displaces by competitive binding the labelled antigen, and labelled antigen enters into the flowing stream. The stream carries the labelled antigen into the conversion stage wherein the enzyme is allowed to react with a substrate in a single or multistep reaction process to produce a measurable product. The product is measured in the detection stage.

Figure 1:
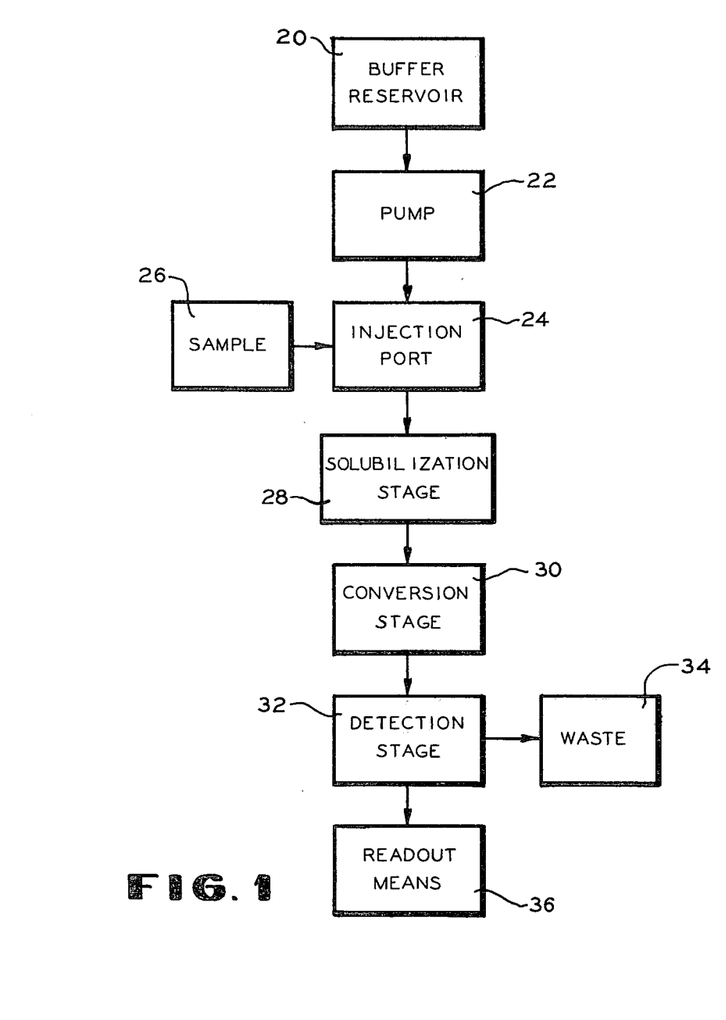
FIG. 1 is a schematic flow diagram according to the method and apparatus of the invention with a solubilization, conversion and detection stage.

The invention will be better understood by reference to FIG. 1. Reservoir 20 contains buffer solution which is pumped by pump 22 to provide a flowing buffer stream. The stream enters injection port 24 which provides means to mix the sample with the buffer stream in the mixing zone defined by the injection port 24. Various antigens contained in biochemical fluids are commonly monitored, e.g. natural compounds such as insulin; and synthetic compounds such as drugs, i.e. phenobarbital and the like. The stream and sample flow into solubilization stage 28, which comprises an antibody, immobilized on a solid support, which will specifically bind the antigen. The antibody on the support has been previously reversibly bound with a saturating amount of an enzyme-labelled antigen, hereinafter enzyme-antigen complex, wherein the antigen is the same one as the antigen in the sample. The antigen in the flowing stream competes with the enzyme-antigen complex in an equilibrium type reaction for available sites on the immobilized antibody. During the equilibrium reaction some of the enzyme-antigen complex is liberated into and is carried along with the flowing stream.

The flowing stream next enters the conversion stage 30 wherein the enzymatically active enzyme-antigen complex reacts with the substrate, i.e. an immobilized starch, of the enzyme and in one or a series of reactions, discussed hereinafter in detail, produces a measurable product which is carried, by the flowing stream, to a detection stage 32 wherein the product is detected and measured. After leaving the detection stage 32, the flowing buffer stream is vented to a waste collector 34. A signal representing the product measured in the detection stage 32 is displayed as a signal in clinically significant units on readout means 36.

It is significant to observe that the enzyme-antigen complex may be enzymatically active when it is bound to the immobilized antibody. Generally, if the enzyme is active when bound it may adversely effect the final measurement. In the present invention, since the enzyme substrate can be introduced after the enzyme-antigen complex is liberated, the activity of the bound enzyme-antigen complex presents no problem. This unique feature is one advantage of the present invention over the known methods of immunoassay.

The above system offers a number of advantages in the detection of antigens in biochemical fluids. First, the antibody, which may be expensive or very difficult to obtain, is immobilized onto a solid support so that desorption into the flowing stream is minimized and the loss of valuable antibody is reduced. This contrasts with present known methods wherein valuable antibody is usually discarded after one analysis. Second, the flow-through stages of the apparatus allow for the easy adaptation of the apparatus to the determination of many types of antigens by the use of the same basic instrument requiring only the interchanging stage components. The individual stages can be readily replaceable cartridges containing the immobilized reagents and adapted to have the buffer stream flow therethrough. Specifically, for example, solubilization stage 28 can include a generally cylindrical cartridge adapted to be inserted into the flowing stream system. The cartridge has a total volume of up to about 40 ml and can be constructed of a plastic composition.

To analyze for a specific antigen, its complementary antibody immobilized in a cartridge is saturated with enzyme-labelled antigen and the cartridge is inserted into the overall apparatus. The flow rate of the buffer stream and antigen containing sample can be adjusted to accomodate the competitive reversible reaction velocity rates and the detection stage 32 adjusted to detect the reaction product from the conversion stage 30.

Figure 2:
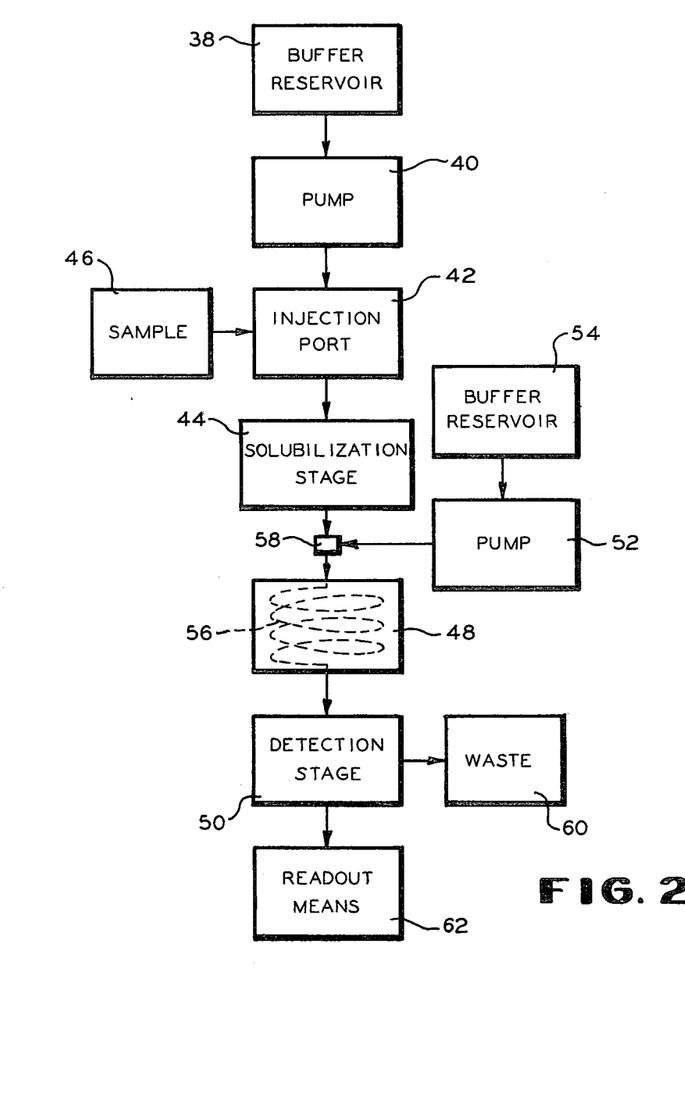
FIG. 2 is a schematic flow diagram essentially similar to FIG. 1 including in addition, a second buffer supply and an alternative embodiment of the conversion stage.

To further demonstrate the utility of the present invention, the following embodiment is a description of the quantitative determination of phenobarbital as illustrated in FIG. 2. Components corresponding to the buffer reservoir 38, pump 40, injection port 42, and solubilization stage 44 as in FIG. 1 are common to all embodiments. In the determination of a phenobarbital sample 46, a phenobarbital antibody is immobilized on a solid support, for example Ultrogel, packed into the cartridge of solubilization stage 44. The antibody is saturated with the enzyme-labelled antigen complex. In this case, the enzyme is glucose-6-phosphate dehydrogenase (GPD), and the immobilized antigen is the phenobarbital. The cartridge is placed into the flowing stream from the buffer reservoir. As the flowing stream containing the sample 46 passes through the solubilization stage 44, some of the enzyme-labelled antigen complex is liberated and flows into conversion stage 48.

The conversion stage 48 and detection stage 50 comprise the most flexibility in the apparatus. In the case of phenobarbital linked GPD, the conversion stage 48 comprises an elongated coiled tube 56 (shown in phantom) which has a long path prior to the arrival of the sample at the detection stage. The tube path is long enough to allow enzyme magnification by the prolonged exposure of the enzyme to the substrate, the glucose-6-phosphate in the tube path. In conversion stage 48, the phenobarbital-GPD complex reacts with the glucose-6-phosphate according to the reaction:

Glucose-6-phosphate + $NAD^+$ → 6-phosphogluconic acid + NADH. This reaction requires glucose-6-phosphate and nicotinamide adenine dinucleotide ($NAD^+$) and produces reduced $NAD^+$, i.e. NADH, which is the product which is measured in the detection stage.

The substrate can be used in the system by mixing it with the buffer in reservoir 38 and having it constantly present in the flowing stream. It can also be introduced just after the flowing stream exits the solubilization stage 44 by the use of a second pump 52 and a second reservoir 54. Also, to obtain a proper solution mix, a magnetic mixer 58 can be included in the fluid stream line. The flowing stream is again vented to waste 60 after the detection stage, and the obtained signal at detection stage 50 is displayed by readout means 62.

The $NAD^+$ may be used interchangeably with $NADP^+$, if their concentrations are properly adjusted in the stream. Generally, it is preferred that the buffer stream carry the substrate from the buffer reservoir 38 through the system to avoid the added expense of a second reservoir 54 and pump 52. However, if the antigen-enzyme complex is still partially enzymatically active while bound to the antibody, it may become necessary to add the substrate and $NAD^+$ after the antigen-enzyme complex is in solution. This prevents product generation by antibody-bound antigen-enzyme complex, which could produce incorrect high readings. The preferred buffer for the system in either case is THAM [tris (hydroxymethyl) aminomethane] at about pH 7.9–8.

The detection stage 50 in the embodiment of FIG. 2 is an optical spectrophotometer equipped with a thermally regulated flow cell, for example a Gilford Instruments Labs, Inc., Model 300N. This spectrophotometer monitors the concentration of the resultant NADH which gives a quantitative measure of the antigen-enzyme complex, and which measure is proportional to the concentration of the phenobarbital antigen in the original sample.

The conversion stage 48 includes a length of chemically resistant tubing 56. The tubing can be coiled and retained as a coil in the cartridge. The extra length of flow path through the coiled tubing allows the antigen-enzyme complex sufficient exposure to the substrate to allow conversion of sufficient substrate to the measurable product to give a reliable reading by the detector in detection stage 50.

The conversion stage 48 in its simplest embodiment is a simple tubing coil 56 so as to increase enzyme exposure to the substrate.

Figure 3:
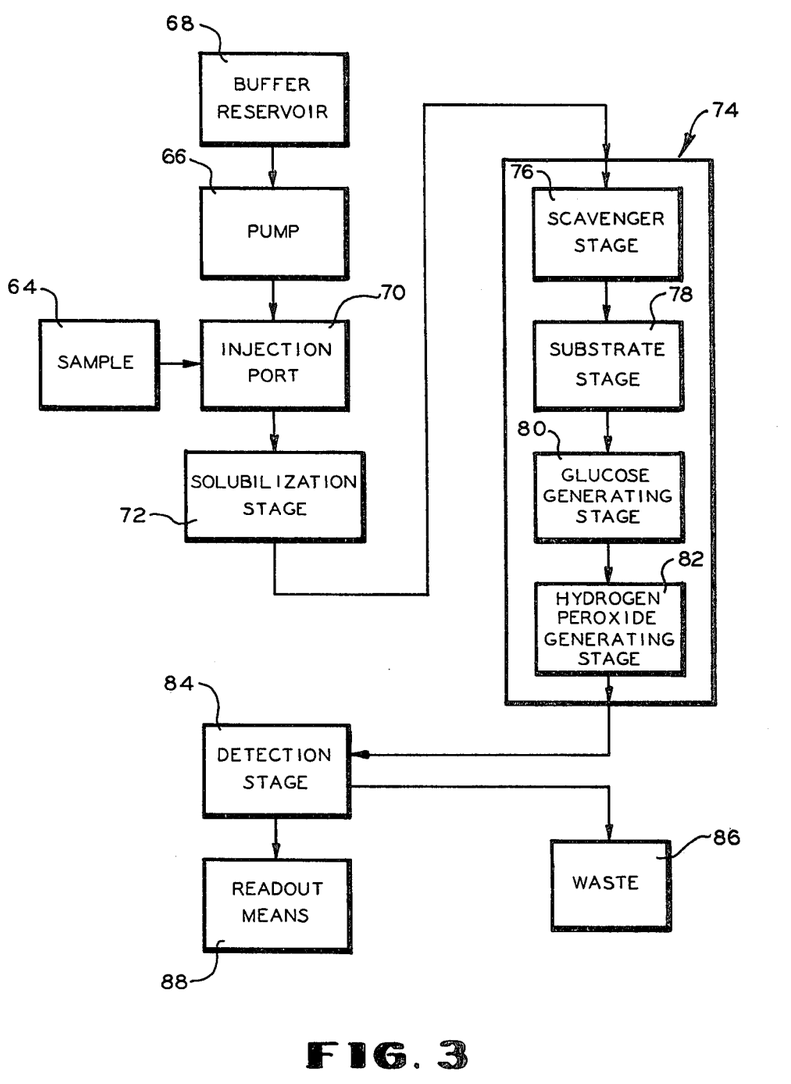
FIG. 3 is a schematic flow diagram essentially similar to FIG. 1 disclosing a second alternative embodiment of the conversion stage.

Another clinically important antigen, insulin, can be determined in another embodiment of the present invention as illustrated in FIG. 3. The basic instrument of the embodiment in FIG. 1 is employed, but the conversion stage is a modification of that used in FIG. 2 to accommodate the particular characteristics of insulin. It is known that insulin can be covalently coupled to glucoamylase (GLA) to form an insulin-GLA complex.

A sample 64 containing insulin is injected through injection port 70 into the flowing stream, established by pump 66 and buffer reservoir 68. The sample and the stream flow into a solubilization stage 72 wherein immobilized antibody to insulin is present. The insulin antibody has been saturated with an enzyme-labelled antigen, i.e. insulin-GLA complex. As the sample 64 flows through the solubilization stage 72 some of the insulin-GLA complex is liberated into the flowing stream in proportion to the concentration of free insulin originally present in the sample 64.

The conversion stage 74 in this embodiment comprises multistage which include a scavenger stage 76, a substrate stage 78, a glucose generating stage 80, and a hydrogen peroxide generating stage 82. The outlet from the hydrogen peroxide generating stage 82 is connected to the detection stage 84 from which the flowing stream vents to waste 86, and the signal detected is transmitted to readout means 88.

Recalling that the insulin is coupled to the enzyme GLA as a complex, the conversion stage 74 is designed to obtain relatively interference free quantification of the insulin-GLA complex, which gives a measure of the concentration of the insulin in the original sample.

The multistage conversion stage operates as follows. The flowing stream containing insulin-GLA complex from the solubilization stage flows into scavenger stage 76 wherein any free glucose that may be contaminating the flowing stream can be removed. Removal of substantially all of any contaminating glucose before determination of the amount of the insulin-GLA complex present is very important, since as will be seen hereinafter, the glucose can cause an erroneous final readout value. Accordingly, the rate of flow of the stream through the scavenger stage 76 can be adjusted as required. The scavenger stage 76, preferably comprises two distinct enzyme reactions comprising the reaction of the contaminating glucose with a glucose oxidase-catalase reagent, whereby the glucose is converted to gluconic acid and hydrogen peroxide by the glucose oxidase of the reagent and the hydrogen peroxide is converted to water and oxygen by the catalase of the reagent. As discussed hereinafter, because hydrogen peroxide is the ultimate product produced as a result of the insulin-GLA reactions it is necessary to make certain that the hydrogen peroxide produced from the contaminating glucose is converted to water and oxygen so that it will not cause erroneous results in the final readout value. To assure complete removal of the hydrogen peroxide, the stream can be passed through additional highly purified catalase stages if necessary. Additionally, different loading fractions of the glucose oxidase and catalase in the scavenger stage 76 can accomplish the desired result.

The stream from the scavenger stage 76, free from interfering glucose and hydrogen peroxide, is in a condition where the insulin-GLA complex contained in the stream can be quantitatively determined. This is done by reacting the insulin-GLA complex in the sample with an immobilized substrate in substrate stage 78. In this embodiment a starch is used for reaction with the complex to quantitatively produce starch fragments, i.e. oligosaccharides, which are a proper index of the measurable insulin-GLA complex activity. The insulin-GLA complex reacts with and breaks down starch molecules into oligosaccharides and the starch desirably should be one which has a high reaction rate with the GLA portion of the complex.

Based on experimentation with various starches, it was found that a starch high in amylose, having mostly straight chains, and containing lower numbers of branched segments is best suited for the starch substrate. Thus, a starch containing almost completely straight chain alpha-1,4-glucosidic linkages is preferable. However, the starch should also be capable of being hydrolyzed by the GLA of the complex to produce oligosaccharides of the desired composition and length, and the starch should be free of materials which can cause competitive enzyme reactions or which interfere with the hydrolysis of the starch by the GLA.

It was found that wheat, corn and potato starches are among the starches which are preferably used as the substrate in this invention. Particularly preferred is potato starch, because it is relatively inexpensive, can be obtained in high purity, resists clumping, and has a high ratio of amylose to amylopectin, containing about 75-85% amylose. Potato starch was also found to be totally hydrolyzed by GLA, producing oligosaccharides which are 2-6 monomers of glucose, with maltose being predominant. The properties and characteristics of potato starch are well suited for the procedures of this invention and it was found that the high ratio of the amylose to amylopectin gives a long life in use as a substrate reagent. Furthermore, potato starch gives higher yields of measurable glucose from the reaction with GLA.

The stream from the substrate stage 78, containing the oligosaccharides, flows to an immobilized glucose generating stage 80 wherein the oligosaccharides are converted to glucose by a glucose generating reagent which must be capable of converting as much of the oligosaccharides to glucose during the flow time through the stage as is practically possible. This is accomplished by careful choice and loading of the enzyme in the stage. In addition, the reagent should be suitably immobilized so that it does not leach into the flow stream of the sample.

Several effective glucose generating reagents are available as a reagent in this flow-through procedures of this invention, for example, immobilized GLA (E.C. 3.2.1.3) or maltase (E.C. 3.2.1.20). The factors involved in selecting the glucose generating reagent are stability, reactivity, ease of handling, and ease of purification. Maltase is presently difficult to purify relative to GLA.

GLA on the other hand is able to degrade many naturally occurring disaccharides and oligosaccharides completely to glucose, i.e. it hydrolyzes both the $\alpha$-1,4-, and $\alpha$-1,6-glucosidic linkages. This enzyme is easy to handle, to purify and is able to react quite effectively with the incoming oligosaccharides in the stream.

The stream containing the glucose generated in the glucose generating stage 80 next flows to the hydrogen peroxide generating stage 82 which contains preferably, immobilized glucose oxidase. The glucose oxidase converts the glucose to hydrogen peroxide and gluconic acid. The glucose oxidase can be purified and immobilized as disclosed in the Examples below. The hydrogen peroxide produced is directed to an electrochemical cell in detection stage 84, which is physically separated from the final immobilized enzyme stage 82.

With respect to the immobilization supports, to be used in the method of the present invention, porous particulate alumina is preferred and has been used with good results as the solid support for all protein immobilizations in the conversion stage 74. Generally, in preparation, the particulate alumina is washed with distilled water after having been sieved with an appropriate size sieve. The particles are preferably on the order of about 0.1 to 0.2 microns average diameter, with a high cavity content so as to increase the loading mass of enzyme per unit mass of support. The washed support is placed under 6 M HCl for about two hours. This procedure appears to activate the alumina to facilitate deposition of the proteins. The activated alumina is again washed and dried. The resultant alumina can be stored under distilled water and a suitable buffer, or can be used at once.

It was found that the porous particles or the porous matrix having a volume porosity in the range of 10 percent to 80 percent, and preferably in the range of 15-50 percent, are very suitable for use in the present invention. The pore size of the support should have pores large enough to allow diffusion of the enzyme into the pores to be deposited in the inner surfaces of the particles of the support. Average pore size diameters of the porous particulates in the range of about 0.01 micron to 10 microns are suitable for most applications with about 0.01 to 2 being preferred for efficiency and economy.

Other suitable porous particulate supports are refractory ceramic oxide powders such as zirconia powder, magnesia powder, silica powder, thoria powder, glass powder, powdered clay, powdered talc, and the like. The particle size of the porous particulates is not critical, although a size range of about −5 to +400 mesh is practical. For efficiency and economy, the size fraction of about −20 to +100 mesh (U.S. Sieve) can be used.

The porous, inert, rigid, dimensionally stable, fluid permeable, membrane supports of refractory oxides can be prepared by compacting the refractory oxide powders to form a "green compact" of the desired configuration such as bars, sheets, etc. The green compacts are then fired for a period of time, and at a suitable temperature sufficient for sintering so as to yield porous refractory supports. The sintering should not be conducted at temperatures or for periods of time which would cause a collapsing or coalescence of the particles so as to form a nonporous body. A convenient indication of the degree of sintering is a comparison of the actual density of the fired compact as compared to the theoretical density of the oxide being fired. Of the many oxides which can be used in the present invention alumina is preferred because of its chemical durability and ease of fabrication.

In forming the support from a powdered refractory oxide, a powdered particle size is selected to yield a sintered compact having a porosity and pore size in the range set forth above. The techniques for compacting and sintering of the porous supports are well-known in the art. Generally, the compacting pressures are in the range of about 1,000 psi to 10,000 psi and sintering temperatures in the range of about 1,000° to 1,700° C. are commercially expedient. Additional details on compacting and sintering of refractory oxides are set forth in the book *Oxide Ceramics*, by E. Ryshewitch, published in 1960 by Academic Press, New York, N.Y.

All of the reagents used in stages 76, 78, 80 and 82 are preferably immobilized on solid supports. In many cases, the immobilization can take place on polysaccharide supports or refractory inorganic oxides, for example, alumina. In many cases the enzymes can be crosslinked to each other after deposition on a support or can be covalently linked to the inorganic support.

The hydrogen peroxide generated in the hydrogen peroxide generating stage 82, as shown in the conversion stage 74 of FIG. 3, is passed through a detection stage 84 comprising, for example, a polarographic cell, preferably containing a three electrode system, which furnishes a cell current which is a quantitative measure of the hydrogen peroxide under test in the cell and thus of the insulin contained in the sample 64. In copending application Ser. No. 477,922, filed June 10, 1974, there is disclosed a method and apparatus for analysis of glucose by oxidation thereof in a bed of immobilized glucose oxidase. The procedures and detection means set forth therein are incorporated herein by reference and can be used in this detection stage for the generated glucose. U.S. Pat. No. 3,957,592 discloses an apparatus and method for the measurement of a cell current using a polarographic cell which is suitable and adaptable for use with the procedure herein to measure the generated glucose in relation to the quantitative amount of antigen in the original sample.

U.S. Pat. No. 3,902,970 discloses another detection cell usable herein, for the measuring of the concentration of glucose in solution, wherein generated hydrogen peroxide is measured in an amperometric cell. The cell has a small bore flow path and includes a cylindrical measuring electrode which carries the sample through its relatively long narrow bore, a counter electrode, reference electrode and a differential amplifier for automatically adjusting the current between the counter and measuring electrodes to maintain the potential between the two electrodes at a predetermined value as fed to one input to the amplifier. The current from the measuring electrode is measured as an indication of the concentration of generated hydrogen peroxide in the stream and thus the glucose concentration generated in the glucose generating stage.

In addition to the use of amperometric type detection cells, other suitable types of detection means can be used herein for the measurement of the generated hydrogen peroxide. In particular, a spectrophotometer can be used, as set forth below, in the detection stage for measuring the generated hydrogen peroxide.

The various reagents reacting with the stream containing the complex can be immobilized in the various stages. Any of the known methods for immobilizing the enzyme reagents on an insoluble support to form a bed of immobilized reagent can be used in this invention. For example, the glucose oxidase used in the scavenger stage 76 and the hydrogen peroxide generating stage 82 can be covalently coupled to a porous glass or alumina support with an amino-functional silane coupling agent as disclosed in the article entitled "Immobilized Enzymes: A Prototype Apparatus For Oxidase Enzyme In Chemical Analysis Utilizing Covalently Bound Glucose Oxidase" by M. K. Seibel et al appearing in Analytical Biochemistry, 52, 402–414 (1973); glucose oxidase can be immobilized on column packing as in the article entititled "A New Principle of Enzymatic Analysis" by H. V. Bergmeyer and A. Hage appearing in Z. Anal. Chem. 261, 333–336 (1972). Other immobilization techniques are also known in the art.

In the scavenger stage 76, as shown in FIG. 3, the glucose oxidase and catalase may be coimmobilized on a suitable support in a flow-through cartridge by the above methods. Similarly, enzymes in the glucose generating stage, the glucoamylase or maltase, can be immobilized as set forth below.

Preferably, the enzyme reagents of this invention are immobilized by cross-linking them onto porous acid-activated alumina because these immobilization techniques have been well developed and their ease of operation are well-known. The alumina exhibits high durability with moderate reagent-load capacity, allowing the high flow-rates requires for fast analysis of samples in the flow-through procedures of the invention.

In addition, the following patents disclose various immobilization techniques usable in this invention: U.S. Pat. No. 3,933,589 issued to Melvin H. Keyes, Jan. 20, 1976 entitled "Chemical Immobilization Of Enzymes;" U.S. Pat. No. 3,839,175 issued to Melvin H. Keyes, Oct. 1, 1974 entitled "Electrodeposition of Enzymes;" and U.S. Pat. No. 3,869,486 issued to Melvin H. Keyes et al, Jan. 14, 1975 entitled "Immobilizing Enzymes With Polystyrene Derivatives." Thus, in forming the bed of immobilized enzyme the selection of the support from materials such as porous glass, particulate and preferably porous refractory oxides such as alumina, titania, zirconia, silica, magnesia, talc, and thoria; glass frit; particulate porcelain; compacted and sintered refractory oxides; clays; water-insoluble polymers; and immobilizing the enzyme thereon by chemical or physical means is well known in the art.

The intermolecular cross-linking of the reagents on an inorganic support, particularly alumina, is preferred because a non-compressible support gives high flow rates for the samples flowing through the analyzer, and is less time consuming, etc.

With respect to the columns, the important requirement is that packed cartridges be permeable to the sample specimen while providing a high surface area to volume ratio to assure adequate contact between the enzyme or substrate reagent and the sample specimen.

The term "antigen" is used herein in its broadest defined meaning to include protein, carbohydrates, enzymes, toxins, drugs, vitamins, etc. which when introduced into the body stimulate the production of an antibody or the like.

The following further illustrate specific procedures used to practice the invention.

EXAMPLE 1

PREPARATION OF SOLUBILIZATION STAGE (Insulin Antibody)

Immobilized antibody to insulin is prepared using an Ultrogel support (or Sephadex or Sepharose) according to the following procedure. The antibody to insulin can be obtained from Pharmacia AB, Uppsala.

A volume of support, with solvent water decanted, is added to an equal volume of distilled water. Because the activation of the support is done with a cyanide compound, the procedure is carried out in a hood. Solid cyanogen bromide, about 50–300 mg per ml of support, is added to the stirred suspension all at once. The pH is quickly elevated to 11 with a sodium hydroxide solution. The base is usually between 2–8 molar for rapid pH modification. The suspension is constantly maintained at 2° C. The reaction occurs in about 10 minutes and no solid bromide should remain. When the solution has finished reacting, ice is added to quickly chill the suspension and the material is filtered through a funnel and rinsed with cold buffer, usually THAM buffer [tris (hydroxymethyl) aminomethane] but always the same buffer as used during the coupling reaction in an amount equal to about 15 volumes of the support.

The antibody solution, usually about 25 mg per 5 ml support in a volume of cold buffer equal to that of the support, is added to the support still in the funnel. The process of filtering and addition of antibody should take less than 90 seconds since the cyanogen activated support is unstable. The mixture is quickly transferred to a beaker, cooled to about 4° C. and very gently stirred for about 20 hours. If the material is handled too roughly or stirred too vigorously, the excellent flow characteristics of the Ultrogel will be lost and the flow characteristics in the cartridge will be destroyed or at least substantially adversely affected.

The resultant material is washed until antibody is no longer washed off, as evidenced by UV absorbance tests.

EXAMPLE 2

PREPARATION OF INSULIN-GLUCOAMYLASE COMPLEX

Insulin antigen is coupled to glucoamylase using a 2.5% solution of glutaraldehyde. Mixed together in a small vial are:

1. 20 U of insulin (0.5 ml of 40 U/ml from Novo Industri A/S, Copenhagen),
2. 7 mg of glucoamylase (0.5 ml of 14 mg/ml from *Rhizopus niveus,* Seihagaken Kogyo Co., Ltd., Tokyo),
3. 25 ml of 1 M potassium phosphate buffer (pH 7.2), and
4. 80 ml of 2.5% glutaraldehyde The mixture is incubated at about 20° C. for about 2 hr. The complex of insulin-glucoamylase is isolated from excess free insulin antigen by column chromatography using a 1×40 cm Bio-Gel P-150 (100 to 200 mesh) which was equilibrated against 0.05 M potassium phosphate buffer, at pH 6.8. The column is eluted with the potassium phosphate buffer and eluted fractions of 1 ml were monitored for protein activity at 280 nm. Generally the isolated insulinglucoamylase complex is pure enough at this stage to enable its use without further processing, for saturating the antibody column. To prepare, the antibody-insulin-glucoamylase composite, the immobilized antibody of Example 1 is poured into a beaker containing deionized water. The purified insulin-glucoamylase complex is added and the material is allowed to incubate. The supernatant is monitored and when the absorbance band due to unbound insulin-glucoamylase vanishes additional insulin-glucoamylase is added, in aliquots, until a persistant absorbance band representing free solution phase insulin-glucoamylase appears. This indicates the antibody is saturated and the procedure is stopped. The support-antibody-insulin-glucoamylase composite is isolated, washed and packed wet into an instrument cartridge. After continued use, the antibody column may be resaturated by slowly flowing a concentrated insulin-glucoamylase solution through the column.

EXAMPLE 3

PREPARATION OF SOLUBILIZATION STAGE (Phenobarbital Antibody)

Immobilized antibody to phenobarbital is prepared using Ultrogel support (or Sephadex or Sepharose) according to the following procedure.

A volume of support, with solvent water decanted, is added to an equal volume of distilled water. Because the activation of the support is done with a cyanide compound, the procedure is carried out in a hood. Solid cyanogen bromide, about 50–300 mg per ml of support, is added to the stirred suspension all at once. The pH is quickly elevated to 11 with a sodium hydroxide solution. The base is usually between 2–8 molar for rapid pH modification. The suspension is constantly maintained at 20° C. The reaction occurs in about 10 minutes and no solid bromide should remain. When the solution has finished reacting, ice is added to quickly chill the suspension and the material is filtered through a funnel and rinsed with cold buffer, usually THAM buffer [tris (hydroxymethyl) aminomethane] but always the same buffer as used during the coupling reaction, in an amount equal to about 15 volumes of the support.

The antibody solution, usually about 25 mg per 5 ml support in a volume of cold buffer equal to that of the support, is added to the support which is still in the funnel. The process of filtering and addition of antibody should take less than 90 seconds since the cyanogen activated support is unstable. The mixture is quickly transferred to a beaker, cooled to about 4° C. and very gently stirred for about 20 hours. If the material is handled too roughly or stirred too vigorously, the excellent flow characteristics of the Ultrogel will be lost and the flow characteristics of the cartridge will be destroyed or at least substantially adversely affected.

The resultant material is washed until antibody is no longer washed off, as evidenced by UV absorbance tests.

EXAMPLE 4

PREPARATION OF PHENOBARBITAL-GLUCOSE-6-PHOSPHATE DEHYDROGENASE COMPLEX

Phenobarbital antigen is coupled to glucose-6-phosphate dehydrogenase (GPD) using a 2.5% solution of glutaraldehyde. Mixed together in a small vial are:
1. 20 U of phenobarbital (0.5 ml of 40 U/ml),
2. 7 mg of GPD (0.5 ml of 14 mg/ml),
3. 25 ml of 1 M potassium phosphate buffer (pH 7.2), and
4. 80 ml of 2.5% glutaraldehyde The mixture is incubated at about 20° C. for 2 hr. The complex of phenobarbital-GPD is isolated from excess free phenobarbital antigen by column chromatography using a 1×40 cm Bio-Gel P-150 (100 to 200 mesh) column equilibrated against 0.05 M potassium phosphate buffer, at pH 6.8. The column is eluted with the potassium phosphate buffer and eluted fractions of 1 ml were monitored for protein activity at 280 nm. Generally the isolated phenobarbital-GPD complex is pure enough at this stage to enable its use without further processing, for saturating the antibody column. To prepare the antibody-phenobarbital-GPD composite, the immobilized antibody of Example 3 is poured into a beaker containing deionized water. The purified phenobarbital-GPD complex is added and the material is allowed to incubate. The supernatant is monitored and when the absorbance band due to unbound phenobarbital-GPD complex vanishes additional complex is added, in aliquots, until a persistant absorbance band representing free solution phase complex appears. This indicates the antibody is saturated and the procedure is stopped. The support-antibody-phenobarbital-GPD composite is isolated, washed and packed wet into an instrument cartridge. After continued use the antibody column may be resaturated by slowly flowing a concentrated phenobarbital-GPD complex solution through the column. The phenobarbital-GPD complex is available from Syva Corp.

EXAMPLE 5

PREPARATION OF THE SCAVENGER STAGE

A. Preparation of the Immobilized Glucose Oxidase

1. Twenty grams of 35% percent porosity, −50 to +60 meshed porous alumina having an average pore size of one-tenth micron, is carefully weighed out.
2. The porous alumina is then washed under twenty five 250 ml aliquots of distilled, deionized water.
3. The washed alumina, from step 2., is then placed under 150 ml of six normal hydrochloric acid in a 200 ml Erlenmeyer flask, for 1 to 1½ hours, swirling gently every ten minutes at room temperature.
4. During the acid-activation of the porous alumina discussed in step 3., the following items are prepared:
   a. A 30 to 40 ml length of dialysis tubing (SPECTRAPOR, trademarked by Spectrum Medical Laboratory) having a molecular weight cut-off limit of 6,000 to 8,000, is obtained and placed in a 200 ml beaker, under 150 ml of 1/100 molar maleate buffer, pH 5.6, and refrigerated at 0° C. to 4° C. for one-half to one hour.
   b. A cross-linking solution is prepared by dissolving two grams of CMC, i.e., 1-cyclohexyl-3-(2-morpholinethyl)-carbodiimide metho-p-tolune solfonate into ten milliliters distilled, deionized water, and stirring it one hour, at room temperature.
   c. Twenty milliliters of glucose oxidase is measured out and is activated by adding twenty-six milligrams succinic anhydride. The resulting mixture is allowed to react for at least forty minutes at room temperature.
5. At the end of the acid-activation time indicated in step (3), above, the alumina is rinsed by rapid swirling under three, one-hundred fifty milliliter aliquots of distilled, deionized water.
6. The alumina is then placed under one-hundred fifty milliliters distilled, deionized water, and deaerated for one hour at room temperature. The flask is swirled gently every ten minutes.
7. At the end of step (6), above, the supernatant solution is carefully decanted off and discarded. To the remaining alumina, the solution prepared in step 4.(b) above is added.
8. A knot is tied in one-end of the dialysis tubing from step 4.(a), above.

9. Into the dialysis bag, the mixture described in step (7) above is added.
10. Then the solution prepared in step 4.(c), above is also added to the dialysis bag, and the open end is then sealed by tying a knot.
11. The closed dialysis bag containing the reactants from step (10) above is then placed under one-hundred fifty mililiters, distilled, deionized water in a two-hundred mililiter flask. This beaker is then placed on a laboratory shaker water bath at zero to six degrees centigrade for twelve to sixteen hours.
12. After step (11) above the material is removed from the dialysis bag, and is washed under one liter distilled, deionized water, and is refrigerated at 0° C. under ten ml of one-one-hundredth molar maleate buffer, pH 6.
13. The activity of the final product is measured: Glucose oxidase activity is measured in a $5 \times 10^{-2}$ M beta-d-glucose solution, buffered to pH 5.6 with 0.01 M acetate buffer. The glucose oxidase activity is found to be 69 U per ml of porous alumina-enzyme composite.

A. Preparation Of Immobilized Catalase

1. Twenty to thirty grams of $-70+80$ mesh porous alumina, as used above, is weighed out and then washed under distilled, deionized water until free of fines. This is followed by a 1 liter rinse with 1 normal hydrochloric acid. This acid-rinsed alumina is then placed under 250 to 500 mililiters of 9 normal hydrochloric acid for 1.5 to 3 hours.
2. At the end of this time, the acid-activated alumina is rinsed with 1 liter of 1 molar hydrochloric acid. The acid rinsed acid-activated alumina is then placed under 0.10 normal hydrochloric acid, and the alumina is evacuated of air by vacuum aspiration for one to two and a half hours.
3. The evacuated acid-activated alumina is then rinsed with 1 liter, 0.01 molar acetate buffer at pH 5.5, and placed under 100 mililiters of 0.01 molar acetate buffer, pH 5.5 and is allowed to swirl on the laboratory shaker, at 0° C. for 0.5 hour.
4. A quantity of crude glucose oxidase is chromatographed on an omega n-decyl amino alkyl hydrophobic gel. The eluant is a mM phosphate buffer pH 6.0. The first catalase containing eluted peak is collected, and retained for immobilization and is added to the final mixture in step 3., above. This mixture was allowed to swirl gently on the laboratory shaker for an additional 0.5 hour.
5. A cross-linking solution is prepared by adding to 10 ml of spectral quality methanol placed in a 100 ml beaker the following reagents, in the order indicated:
   a. two-tenths of a mililiter of diaminopropane.
   b. one-tenth of a mililiter of dibromoethane.
   c. fifteen-hundredths of a mililiter of concentrated hydrochloric acid and
   d. fifty mililiters of 0.01 molar acetate buffer, pH 5.5. The cross-linking solution is then allowed to stir for 0.5 hour on a magnetic stirrer.
6. The contents of step 5., above, are then added to the final contents of the mixture in step 4., above; slowly over a 0.5 hour period. The mixture is then allowed to react overnight at 0° C., while swirling in a water bath on the lab shaker.
7. Then, the final product is washed under 2 to 3 liters of 0.01 molar acetate (0.1 molar in sodium chloride), pH 5.5. The washed product is then stored under 10 to 15 ml of this same buffer, under refrigeration at 0° C.
8. The activity of this material in an 88 mM hydrogen peroxide, 0.01 molar acetate, pH 5.5 substrate-buffer solution is measured by measuring the increase in oxygen content as a function of time; measured from the time the immobilized enzyme is first added to 5 ml of the buffer solution, and the substrate is quickly added. Using this procedure the activity is measured at 58 U of catalase per mililiter of the alumina-catalase composite.

EXAMPLE 6

IMMOBILIZED SUBSTRATE

1. Forty to fifty g of $-40+50$ mesh porous alumina, having an average pore diameter of 0.1 micron, is weighed out and washed with 0.5 to 3.5 liters of distilled, deionized water until free of fines.
2. The washed alumina is then placed under 200 ml of 6 N hydrochloric acid and is allowed to shake on the laboratory shaker for 16 to 24 hours at room temperature (about 27° C.).
3. Five g of amylose (extracted from potato starch) is weighed out and suspended in 100 ml of one milimolar phosphate buffer, pH 6.
4. Five to 15 g of 'wet' immobilized dextranase (E.C. No. 3.2.1.11) is weighed out. The five g of amylose, suspended as in step 3, is then added to the weighed out quantity of immobilized dextranase. This immobilized dextranase-amylose suspension is allowed to react 16–20 hr, at room temperature, at pH 6.0.
5. The starch suspension is then decanted off, and the immobilized dextranase is either discarded, or washed, and retained for later use. This dextranase treatment forms oligosaccharides and fragments from the starch for better immobilization.
6. To the decanted amylose solution is added five ml of 0.3 molar potassium hydroxide. The resulting alkaline amylose suspension is then allowed to gently swirl, on the laboratory shaker for one hour.
7. Then 0.5 ml of diaminopropane is dissolved into ten ml of methanol, as is added to the alkaline amylose suspension. This mixture is then allowed to swirl gently, on the laboratory shaker for one hr. The now acid-activated alumina is then placed on an aspirator to remove air from the pores of the alumina for two hr.
8. The now evacuated acid-activated alumina is then washed with one to 2.5 liters of one normal hydrochloric acid.
9. Then to the washed evacuated acid-activated alumina is added the mixture described in step 7., above. This material is then placed on a laboratory shaker, and is allowed to swirl for one hr., at room temperature.
10. To step 9., above is added an additional five ml of 0.3 molar potassium hydroxide. The resulting mixture is allowed to swirl gently for an additional one hr.
11. During step 10., above a cross-linking solution is prepared by mixing the reagents in the order as indicated in a 50 ml beaker;
   a. twenty-five hundredths of a ml of diaminopropane, into 10 ml of methanol, b. one tenth of a ml of 0.3 molar potassium hydroxide,
c. fifteen hundredths of a ml of dibromoethane, and
d. ten ml of distilled, deionized water.
12. The mixture as prepared in step 11., above is added to step 10. above. The resulting mixture is then allowed to cross-link 16–20 hr at room temperature, while swirling on the laboratory shaker.
13. The product is then washed under two to five liters of one millimolar phosphate buffer, pH 6.; followed by washing under two to five liters distilled, deionized water. The now washed amylose-alumina composite is then stored, under refrigeration at 0° C., in 10 to 20 ml of one millimolar phosphate buffer, pH 6.
14. The amount of amylose immobilized by this procedure is found to be 0.1 g amylose/gram alumina (alternatively expressed as 0.26 gram amylose/milliliter alumina).

EXAMPLE 7

IMMOBILIZATION OF THE GLUCOSE GENERATING REAGENT

Twenty-five to 50 g of porous remeshed alumina, −50+60 mesh, was weighed out, washed thoroughly and acid-activated as above. The resulting activated material was placed under 50 ml of 0.01 to 0.05 M acetate buffer, pH 5.6, and set aside for one hour while gently swirling on the laboratory shaker, at room temperature.

During this time about 1500 mg of, (1) crude enzyme (maltase or glucoamylase) was weighed out, and dissolved in 25 ml of distilled, deionized water, or buffer and centrifuged at 10,000 g's for 0.5 hour, or (2) a 40% ammonium sulfate precipitate was collected. In the case of the crude enzymes, the supernatant solution (at least 25 ml) was added to the acid activated alumina, and allowed to absorb onto acid activated alumina for a period of 0.5 to 1.5 hour. However, in the case of the 40% ammonium sulfate precipitation the precipitate was redissolved in at least 25 ml of distilled, deionized water, or buffer (0.01 M acetate, pH 5.6), and allowed to adsorb onto the acid-activated alumina for 0.5 to 1.5 hour.

After the adsorption process had been completed, a cross-linking reagent composed of diaminopropane and dibromoethane, as in Example 6, was prepared and added. The reaction was allowed to continue 16 to 20 hr., at room temperature, while swirling on the laboratory shaker. Washing and storage are done as above described.

EXAMPLE 8

PREPARATION OF IMMOBILIZED GLUCOSE GENERATING REAGENT

Preparation Of Immobilized Purified Glucoamylase

1. Twenty grams −70+80 mesh, rescreened, porous alumina is weighed out, and first washed under distilled, deionized water until free of fines, and then washed under 500 ml, 1/10 M hydrochloric acid.
2. Fifty grams crude glucoamylase is dissolved in 100 ml of 1/100 M phosphate buffer, pH 6, and centrifuged at 12,300 gravity forces for one hour in a ultra centrifuge. The resulting supernatant is decanted off and saved. The resulting insoluble precipitate is discarded.
3. The supernatant from step 2., above, is chromatographed on a Sephadex G-200 column (6 cm×0.7 cm) at a flow-rate of 136 ml per hour. The entire second peak fraction, as it is eluting off, is selected for immobilization.
4. The washed alumina of step 1., above, is then placed under 250 ml of 9 normal hydrochloric acid and is allowed to swirl, undisturbed, at room temperature for 1.5 hr.
5. The alumina is then washed twice, under 500 ml of 1/10 M hydrochloric acid followed by a 500 ml aliquot wash of 1/100 M phosphate buffer, pH 6.
6. The washed alumina is then placed under 50 ml of 1/100 M phosphate buffer, pH 6 and is allowed to swirl, undisturbed, for at least one-half hour at room temperature on a laboratory shaker.
7. To the mixture prepared in step 6., above, is added the entire contents of step 3. above.
8. The mixture prepared in step 7., above, is allowed to swirl undisturbed for one hour, at room temperature.
9. Into 15 ml 1/100 M phosphate buffer, pH 6, is added.
    a. five milliliters spectral quality methanol
    b. 5/100 ml diaminopropane
    c. 2/100 ml dibromoethane, and
    d. 5/100 ml concentrated hydrochloric acid.
10. The cross-linking mixture prepared in step 9, above, is added to the mixture of step 8., above, in equal volume aliquots over a half hour period.
11. The resulting mixture from step 10., above, is then allowed to react for 12 to 16 hours, at room temperature.
12. The final product is washed, and stored as above.
13. The activity of this preparation is measured as 8 Units of glucoamylase per milliliter alumina-glucoamylase composite, in a 1/100 M maltose substrate solution, buffered to 1/100 M in acetate buffer, pH 5.5.

EXAMPLE 9

PREPARATION OF THE HYDROGEN PEROXIDE GENERATING REAGENT

1. Thirty grams −60+70 mesh, resieved through an eight mesh wire screen for five minutes, porous alumina is carefully weighed out, and washed under one liter distilled, deionized water.
2. The alumina is placed under 200 ml of six normal hydrochloric acid for one hour while swirling, and left undisturbed for one hour.
3. Twenty ml glucose oxidase is prepared as in Example 5.
4. Ten milligrams of succinic anhydride is dissolved in 1 ml of acetone.
5. Three-tenths milliliter of the solution prepared in step 4., above is added to the enzyme solution of step 3., above every 10 minutes, and allowed to react undisturbed for 20 minutes after all the solution of step 4., above has been completely added.
6. The material of step 2., above is then washed under distilled, deionized water, until the supernatant is clear.

7. The alumina is then placed under 200 ml distilled, deionized water and deaerated for at least one hour. The supernatant solution is then discarded.
8. The solution of step 5., above, is then added to the alumina of step 7., above, and the pH is adjusted to 4.2.
9. One-tenth gram EDC, i.e, 1-ethyl-3-(3-dimethylaminopropyl) carbodiimide hydrochloride is added to step 8., above. After a half hour reaction period, the pH is adjusted to 5 with sodium hydroxide.
10. Four-tenths of a gram of EDC, is dissolved in 30 ml distilled, deionized water, and added to step 8., above at a rate of 1/10 ml per minute.
11. The solution of step 10., above is allowed to react for 12 to 16 hours, on the laboratory shaker, at 0° C.
12. The final product is washed and stored.
13. The activity of this preparation is measured as 24 Units glucose oxidase per milliliter alumina-glucose oxidase composite, in a 0.01 molar acetate buffer-substrate solution, pH 5.5, with no detectable amounts of catalase activity.

EXAMPLE 10

A continuous stream quantitative determination of the antigen phenobarbital in a sample may be accomplished using the apparatus according to the present invention. The apparatus shown in FIG. 2 is equipped with a solubilization stage 44, comprising a cartridge of approximately 8 ml total volume and a sample 46 of approximately 0.1 ml is injected into a flowing aqueous buffer stream. The stream contains 55 mM THAM buffer, [tris(hydroxymethyl)aninomethane] at about pH 8, 0.6 mM NAD, 0.1 mM glucose 6-phosphate, and approximately 1% Bio-Ban, as a bacteriostat. The sample is injected into the stream through the injection port 42 and is carried by the flowing stream to the solubilization stage 44. The solubilization stage comprises immobilized phenobarbital antibody, immobilized according to Example 3 and saturated with phenobarbital-glucose-6-phosphate dehydrogenase (GPD) complex.

As the stream and sample flow through the solubilization stage the phenobarbital of the sample competitively binds with the antibody thereby releasing phenobarbital-GPD complex into the stream. The phenobarbital-GPD complex in the stream flows from the solubilization stage into the conversion stage 48. The conversion stage comprises a few feet of chemically resistant tubing to delay the arrival of the phenobarbital-GPD complex at the detection stage for a sufficient period of time to allow enzyme magnification of the glucose-6-phosphate contained in the flowing stream. The flow rate throughout the procedure is about 1 ml per minute.

After leaving the conversion stage the phenobarbital-GPD complex flows into the detection stage. In this embodiment the detection stage is a spectrophotometric signal detector calibrated for a 340 nm absorbance measurement. The Model 300 N Micro-Sample Sepctrophotometer equipped with a thermally regulated flow cell from Gilford Instrument Labs., Inc., is suitable for the detection of the phenobarbital-GPD complex. The signal absorbance generated by the phenobarbital-GPD complex is directly related to the quantity of phenobarbital contained in the original sample. Typically phenobarbital concentrations are on the order of 10 to 75 mg per liter of sample.

EXAMPLE 11

A 0.1 ml sample containing an unknown quantity of insulin is injected into the flowing aqueous buffer stream according to the apparatus shown in FIG. 3. The sample 64 is contaminated with approximately 20–100 mg of free glucose. The stream flows at a rate of approximately 10 ml per hour, and contains 55 mM THAM buffer, [tris(hydroxymethyl)aminomethane] and has about 1% Bio-Ban bacteriostat about pH 8. After injection of the sample into the flowing stream at the injection port 70, the sample is carried into a solubilization stage 72 by the stream.

The solubilization stage comprises an immobilized insulin antibody, prepared according to Example 1. The insulin antibody is saturated with insulin-glucoamylase (GLA) complex. The solubilization stage comprises a cartridge column containing approximately 40 ml total volume. As the stream and sample flow through the solubilization stage, the free insulin in the sample competes with the insulin-GLA complex and liberates insulin-GLA complex into the flowing stream.

The stream and complex then flow into the conversion stage 74. The first stage within the conversion stage is the scavenger stage 76. In the scavenger stage, Reaction 1 takes place as follows:

1. Scavenger Stage

The glucose free stream and sample containing the insulin-GLA complex then flows into a substrate stage 78. In the substrate stage, Reaction 2 takes place:

2. Substrate Stage

The stream containing the GLA generated oligosaccharides flows into the glucose generating stage 80. In the glucose generating stage, Reaction 3 takes place:

3. Glucose Generating Stage

The generated glucose from the sample in the stream flows into hydrogen peroxide generating stage 82 wherein Reaction 4 takes place, and then into the detection stage 84 wherein Reaction 5 takes place:

4. Hydrogen Peroxide Generating Stage

5. Detection Stage $$H_2O_2 \xrightarrow{\text{polarographic cell}} H_2O + O_2$$

In this embodiment, the detection stage is a three electrode electrochemical cell in which the hydrogen peroxide is quantitatively determined by generating a signal in the detection stage, which communicates the signal to readout means, typically a digital display panel calibrated in milligram percent to represent the quantitative amount of initial insulin antigen in a sample.

What is claimed is:

1. A method for quantitatively determining the amount of an antigen contained in a biochemical fluid comprising obtaining sample of said fluid and mixing it in a mixing zone with an aqueous solution, passing said sample-solution into a solubilization stage containing an immobilized antibody which is specific to said antigen, said immobilized antibody initially having an immunochemically equivalent amount of reversibly bound an antigen-enzyme complex wherein said antigen of said complex is the same as the antigen in the sample, maintaining said sample-solution in said solubilization stage for a period of time and under conditions sufficient for a competitive equilibrium reaction to take place between the said antigen and said bound antigen complex, thereby displacing a quantity of said bound antigen complex from said immobilized antibody into said sample-solution; passing said complex-containing sample-solution into a conversion stage containing a substrate capable of reacting with said enzyme of said complex to produce a measurable reaction product in said sample-solution; passing said measurable reaction product-containing sample-solution into a detection stage wherein said measurable reaction product is quantitatively measured to obtain a reading, and comparing said measured reading to the quantitative amount of antigen in said original sample.

2. The method of claim 1 wherein said original sample is diluted into an aqueous buffered solution prior to passing it into said solubilization stage.

3. The method of claim 1 wherein said antibody is immobilized on a solid support.

4. The method of claim 3 wherein said solid support is a refractory metal oxide.

5. The method of claim 4 wherein said refractory metal oxide is alumina.

6. The method of claim 1 wherein said antigen in said original sample is phenobarbital, said antigen-enzyme complex is a phenobarbital-glucose-6-phosphate dehydrogenase complex, and said antibody is anti-phenobarbital, and said substrate is glucose-6-phosphate.

7. The method of claim 1 wherein said conversion stage comprises an extended confined reaction zone through which said sample-solution is passed.

8. The method of claim 7 wherein said measurable reaction product in said detection stage is read spectrophotometrically.

9. The method of claim 1 wherein said antigen in said original sample is insulin, said antigen-enzyme complex is an insulin-glucoamylase complex, said antibody is anti-insulin, and said substrate is a starch.

10. The method of claim 1 wherein said original sample is contaminated with free glucose which includes flowing said sample through a scavenger stage prior to the production of a measurable reaction product in said sample-solution.

11. The method of claim 1 wherein said original sample is contaminated with free glucose and said conversion stage includes a scavenger stage containing immobilized scavenger reagents capable of reacting with and removing said contaminating glucose, a substrate stage containing an immobilized starch reagent capable of reacting with said complex contained in said sample solution to produce oligosaccharides, a glucose generating stage containing immobilized glucose-generating reagent capable of reacting with said oligosaccharides to produce a glucose reaction product in said sample solution, and a hydrogen peroxide generating stage containing an immobilized reagent capable of oxidizing said glucose reaction product to generate hydrogen peroxide defining said measurable reaction product.

12. The method of claim 11 wherein said hydrogen peroxide is passed to and read in said detection stage in an electrochemical cell.

13. The method of claim 1 wherein said antigen is insulin.

14. The method of claim 1 wherein said antigen-enzyme complex is insulin-glucoamylase.

15. The method of claim 1 wherein said aqueous solution comprises a buffer and said buffered solution is passed as a flowing stream into a mixing zone wherein said original sample is introduced, and wherein said flowing stream containing said original sample is flowed sequentially through said solubilization, conversion, and detection stages.

16. An apparatus for the quantitative determination of an antigen contained in an aqueous biochemical sample, comprising in combination, a reservoir containing a buffer diluent solution, mixing means for said diluent solution and said sample after they are combined, solubilization means to receive the mixed diluent solution and sample containing immobilized antibody initially saturated with an immunochemically equivalent amount of antigen-enzyme complex reversibly bound thereon, conversion means to receive the stream from the solubilization means containing immobilized reagent capable of reacting with said complex to produce a measurable reaction product, detection means capable of monitoring said measurable reaction product to produce a reading relatable to the amount of said antigen.

17. The apparatus of claim 16 wherein said antibody is anti-insulin and said antigen-enzyme complex is an insulin-glucoamylase.

18. The apparatus of claim 16 wherein said antibody is anti-phenobarbital and said antigen-enzyme complex is a phenobarbital-glucose-6-phosphate dehydrogenase.

19. The apparatus of claim 16 wherein said conversion stage comprises elongated, flexible, chemically resistant tubing.

20. The apparatus of claim 16 wherein said detection stage comprises a flow-through design spectrophotometric cell.

21. The apparatus of claim 16 wherein said sample is contaminated with glucose and said conversion stage comprises, in series, scavenger means comprising immobilized scavenger reagent capable of removing contaminating glucose from said sample, substrate means containing an immobilized starch reagent capable of reacting said complex to produce oligosaccharides, glucose generating means containing immobilized glucose generating reagent capable of reacting with said oligosaccharides to produce a glucose reaction product, and a hydrogen peroxide generating means containing immobilized reagent capable of oxidizing said glucose reaction product to hydrogen peroxide.

22. The apparatus of claim 21 wherein said detection means comprises a hydrogen peroxide sensitive electrochemical cell.

23. A method for determining the presence of an antigen in a biochemical fluid, comprising:
  a. contacting a sample of said fluid with an immobilized antibody specific to said antigen, said antibody initially having bound thereto an immunochemically equivalent amount of enzyme-antigen complex, the antigen of said complex corresponding to said antigen,
  b. equilibrating said sample and said immobilized antibody under conditions sufficient to replace enzyme-antigen complex bound to said immobilized antibody with said antigen and thereby liberating a portion of said bound complexes
  c. reacting said liberated enzyme-antigen complex with a reactive substrate to produce a detectable product, and
  d. detecting the presence of said product.

24. The method of claim 23 including a quantitative testing for said predetermined antigen, the amount of said equilibrating being a measure of the presence of said predetermined antigen, and said reaction of said liberated enzyme-antigen complex with the reactive substrate producing a measurable detectable product.

* * * * *